(12) United States Patent
Biscup et al.

(10) Patent No.: US 8,672,983 B2
(45) Date of Patent: Mar. 18, 2014

(54) ORTHOPEDIC PLATE SYSTEM

(75) Inventors: Robert Biscup, Fort Lauderdale, FL (US); Michael Veldman, Memphis, TN (US); Clayton G. Leroux, Westlake, OH (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1504 days.

(21) Appl. No.: 11/522,632

(22) Filed: Sep. 18, 2006

(65) Prior Publication Data
US 2008/0097447 A1  Apr. 24, 2008

(51) Int. Cl.
*A61B 17/58* (2006.01)

(52) U.S. Cl.
USPC .............................. 606/286; 606/267; 606/287

(58) Field of Classification Search
USPC ......... 606/261, 263, 264, 265, 267, 268, 269, 606/270, 271, 272, 305, 328, 273, 274, 280, 606/286–290, 307, 308, 60, 246, 250–260, 606/262, 266, 275–279
See application file for complete search history.

(56) References Cited

U.S. PATENT DOCUMENTS

| | | | |
|---|---|---|---|
| 4,611,581 A | | 9/1986 | Steffee |
| 4,653,481 A | * | 3/1987 | Howland et al. ............... 606/261 |
| 4,655,199 A | | 4/1987 | Steffee |
| 5,084,049 A | * | 1/1992 | Asher et al. .................... 606/251 |
| 5,330,473 A | * | 7/1994 | Howland ....................... 606/250 |
| 5,613,967 A | * | 3/1997 | Engelhardt et al. ........... 606/305 |
| 5,800,435 A | * | 9/1998 | Errico et al. ................... 606/261 |
| 6,136,002 A | * | 10/2000 | Shih et al. ...................... 606/250 |
| 6,206,879 B1 | * | 3/2001 | Marnay et al. ................... 606/53 |
| 6,287,309 B1 | * | 9/2001 | Baccelli et al. ............... 606/292 |
| 6,315,779 B1 | * | 11/2001 | Morrison et al. ............. 606/281 |
| 6,355,038 B1 | * | 3/2002 | Pisharodi ...................... 606/300 |
| 6,379,357 B1 | | 4/2002 | Bernstein et al. |
| 6,435,557 B1 | * | 8/2002 | Palvoelgyi ..................... 280/834 |
| 6,645,207 B2 | * | 11/2003 | Dixon et al. ................... 606/261 |
| 6,689,133 B2 | * | 2/2004 | Morrison et al. ............... 606/71 |
| 2003/0045875 A1 | * | 3/2003 | Bertranou et al. .............. 606/61 |
| 2003/0187438 A1 | | 10/2003 | Assaker et al. |
| 2004/0006342 A1 | * | 1/2004 | Altarac et al. ................... 606/61 |
| 2004/0153092 A1 | * | 8/2004 | Beger et al. ................... 606/104 |
| 2004/0177847 A1 | * | 9/2004 | Foley et al. ................... 128/95.1 |
| 2004/0254577 A1 | * | 12/2004 | Delecrin et al. ................ 606/61 |
| 2005/0216001 A1 | * | 9/2005 | David ............................. 606/61 |
| 2006/0084989 A1 | * | 4/2006 | Dickinson et al. .............. 606/61 |

FOREIGN PATENT DOCUMENTS

| | | |
|---|---|---|
| DE | 198 48 715 | 8/2000 |
| DE | 101 32 712 | 1/2003 |
| FR | 2 832 620 | 5/2003 |
| WO | WO 01/39677 | 6/2001 |
| WO | WO 03/037200 | 5/2003 |
| WO | WO 2006/041845 | 4/2006 |

* cited by examiner

*Primary Examiner* — Jerry Cumberledge

(57) ABSTRACT

An orthopedic medical apparatus and methods are disclosed, among which are a cylindrical orthopedic plate and clamps and fixation members for attaching the plate to tissue such as bone tissue. In one embodiment, the plate includes sides and ends that are cylindrical, and the clamps are adapted to fit thereto. Additional apparatus in the form of a lateral connecting member and a connecting plate usable with the orthopedic plate are also disclosed. Methods for using the disclosed apparatus are also described.

23 Claims, 7 Drawing Sheets

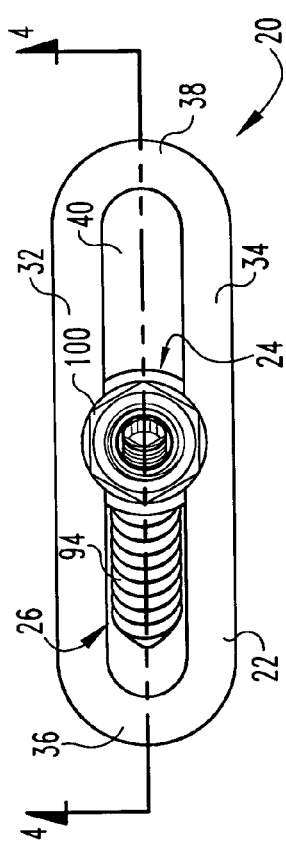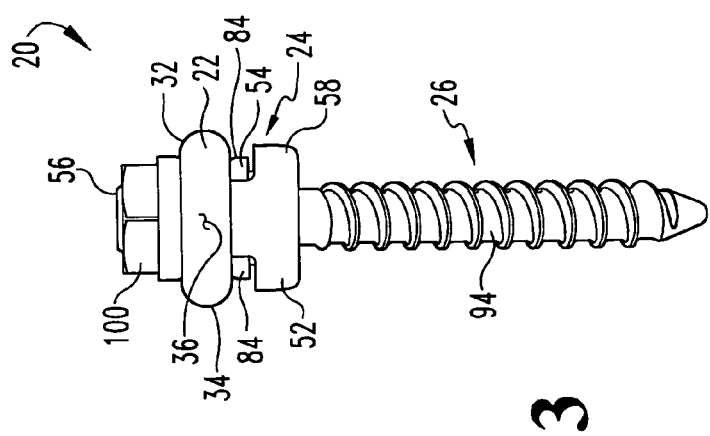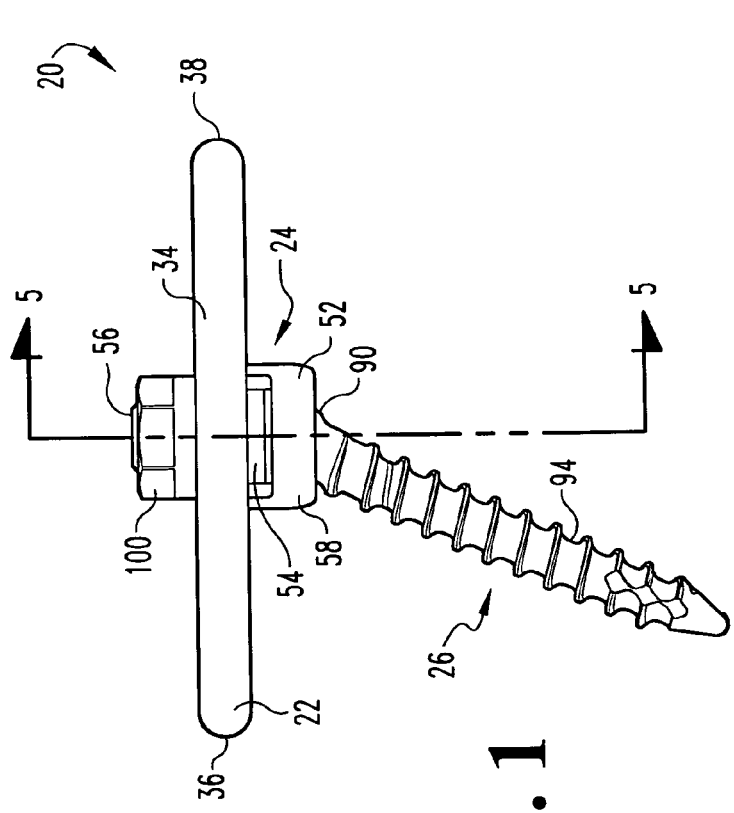
Fig. 2
Fig. 3
Fig. 1

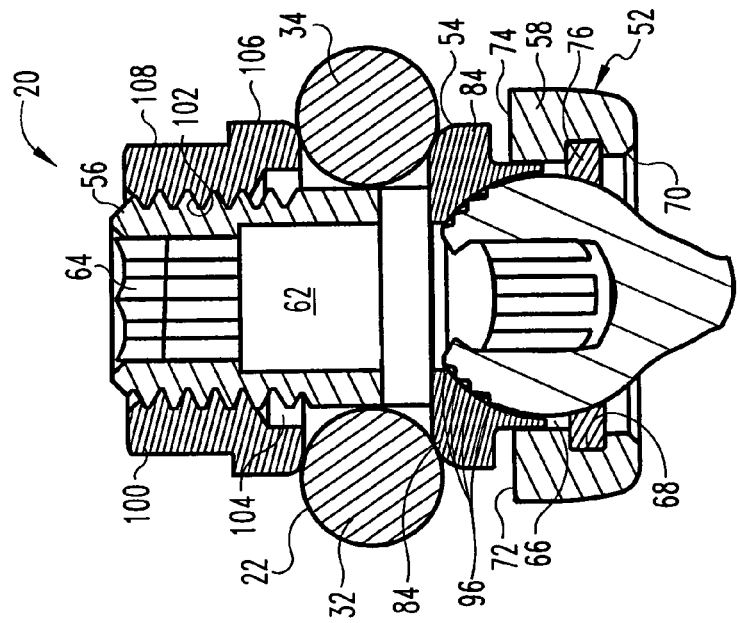
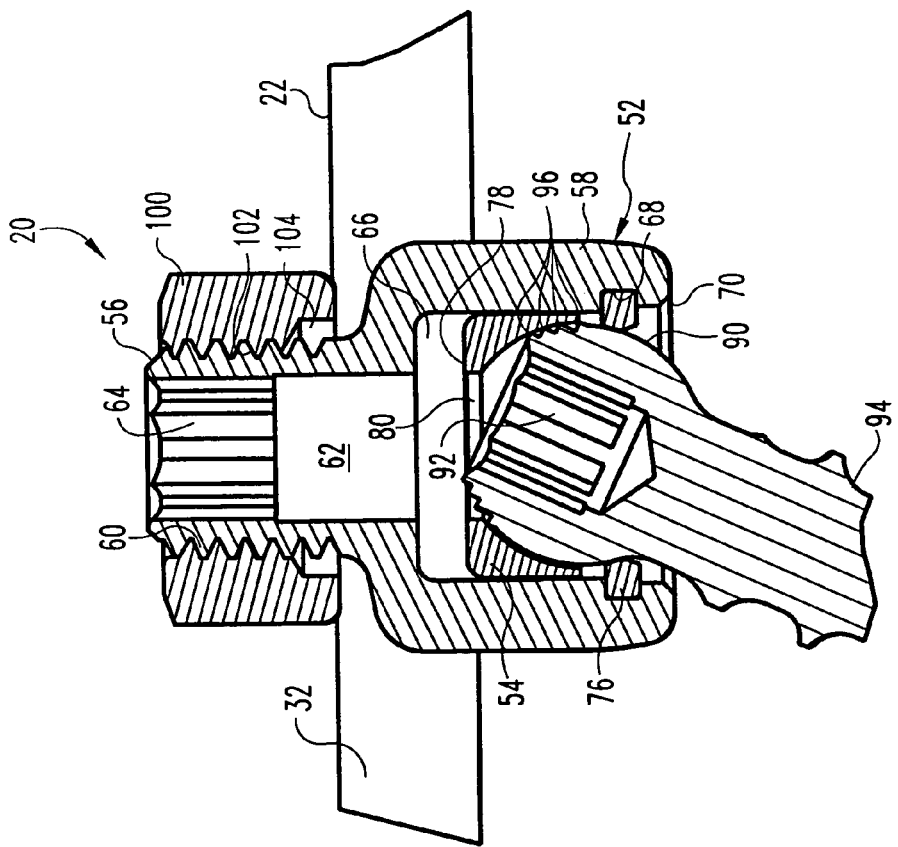
Fig. 5
Fig. 4

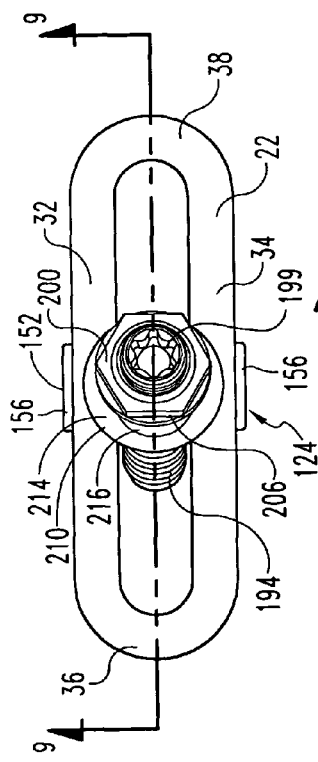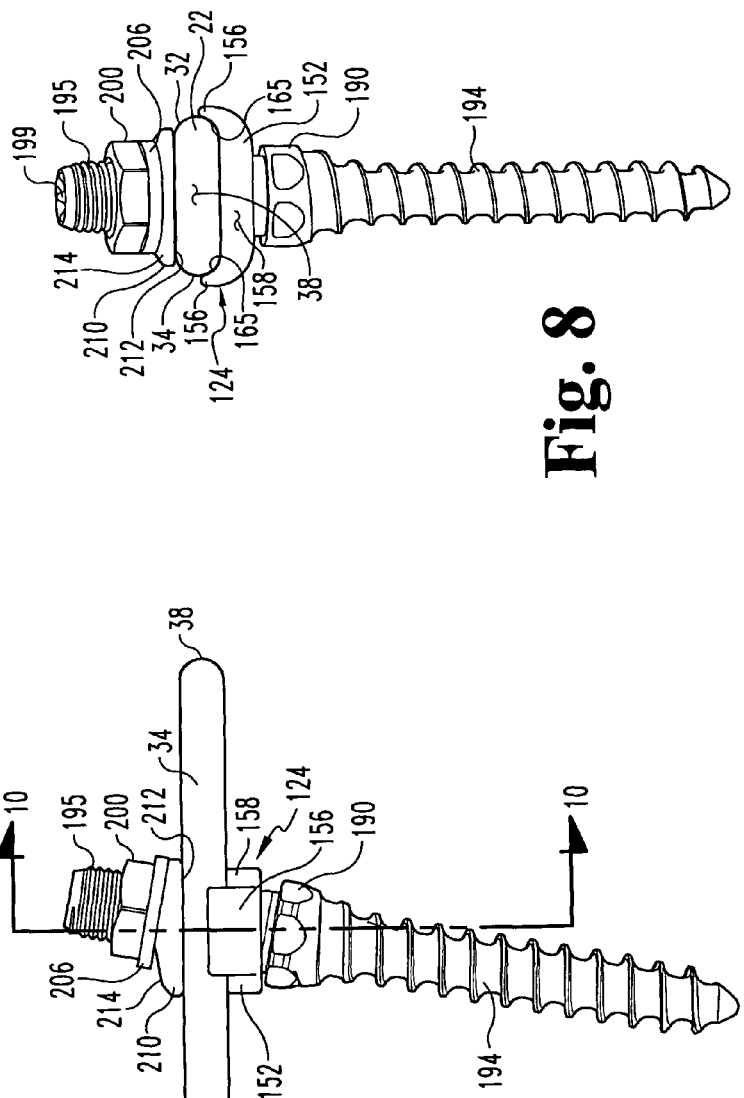

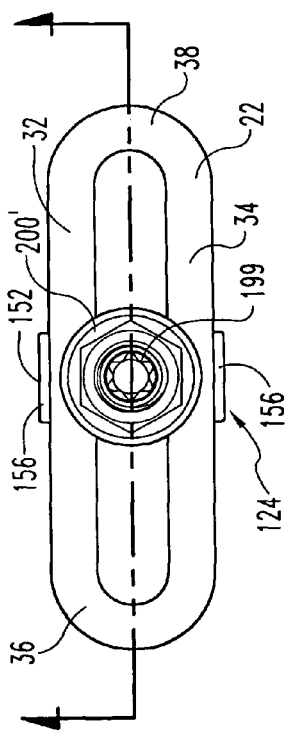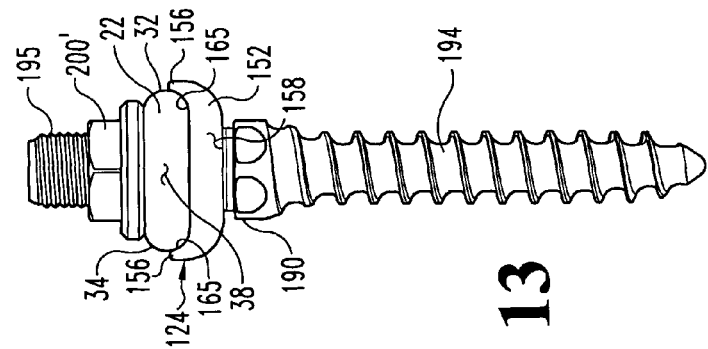

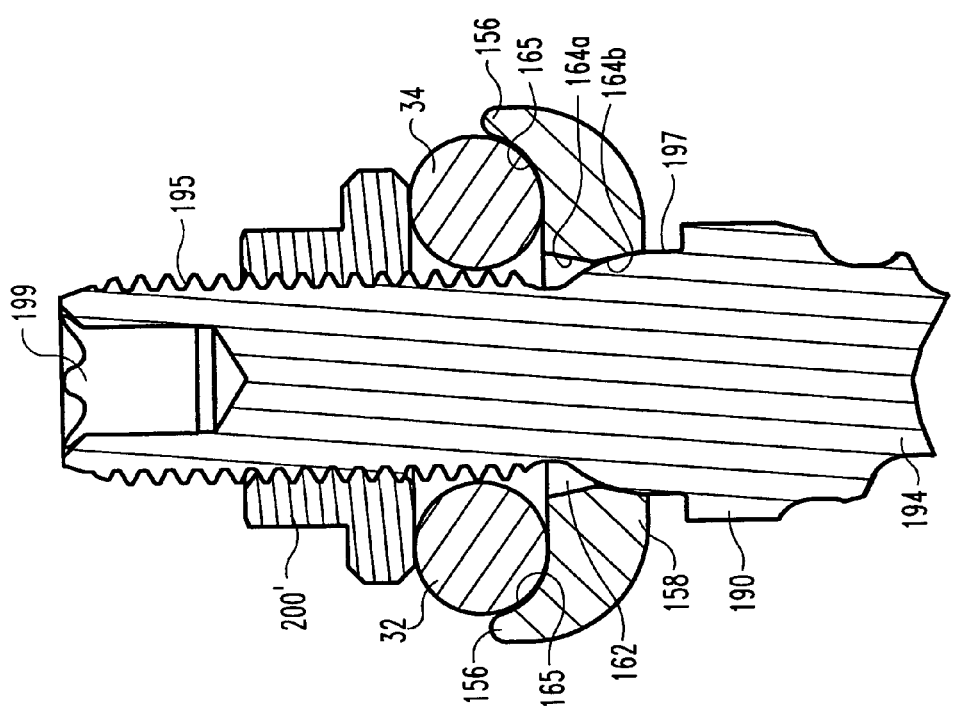
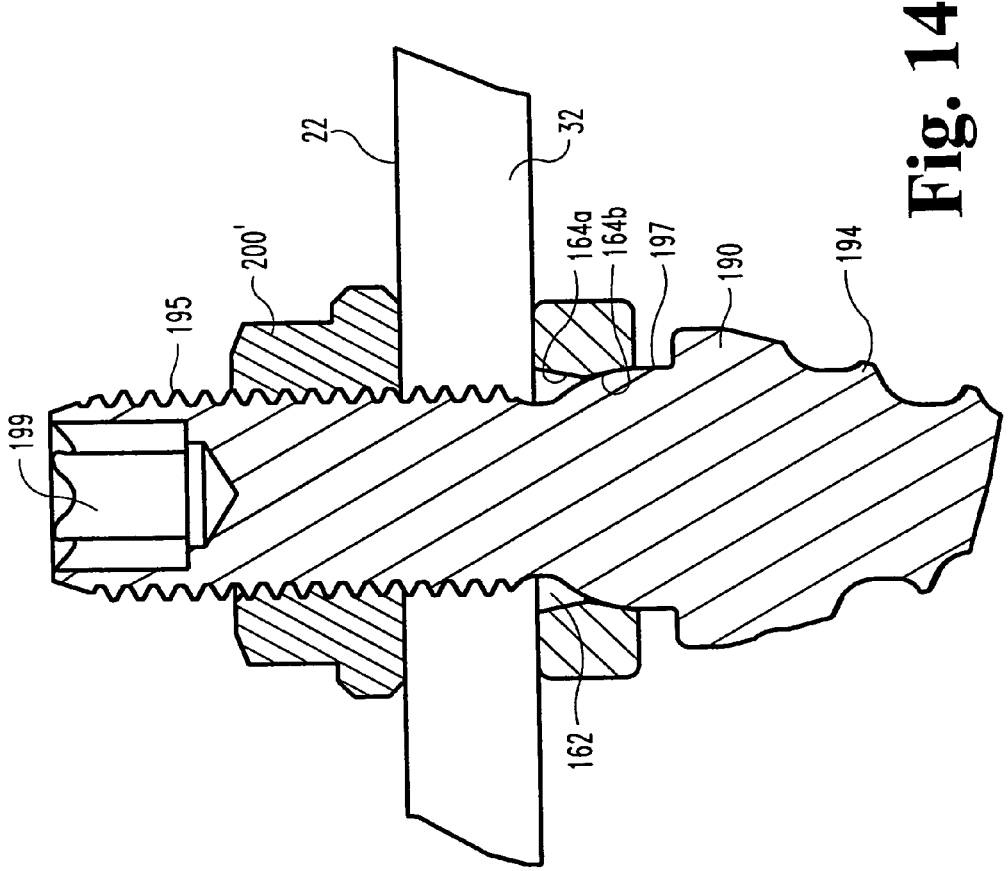

ORTHOPEDIC PLATE SYSTEM

The present disclosure concerns orthopedic implants, such as those for the spine. Specifically, the present disclosure includes a cylindrical plate and bone anchor system, which may be used to treat or correct orthopedic injury, deformation or other problems.

BACKGROUND

In the art of orthopedic surgery, an elongated plate or rod can be fixed to bones in order to hold them and support them in a given position. For example, in a procedure to fuse damaged vertebrae, the vertebrae are positioned in a corrected position as required by the surgeon. A flat plate, i.e. a plate having planar upper and lower sides, is placed adjacent to or against the bone, and bone anchors are employed to secure the plate to the bones. Bone screws or bolts can be used as the bone anchors, and with such anchors placement is accomplished by drilling one or more holes in the bone(s), and threading the anchors into the holes. An anchor can be threaded into a hole through the plate, or the plate can be placed in position around the anchor after threading into the hole. The anchor and plate are secured to each other to prevent relative movement. In this way, bones may be held and/or supported in proper alignment for healing.

Other orthopedic systems use rods to connect to bone anchors and provide stability to tissue such as vertebrae. Such rods may be placed along vertebrae, for example, and contoured so as to hold the bones in a desired position and support them.

DESCRIPTION OF THE DRAWINGS

FIG. 1 is a side elevational view of an embodiment of an orthopedic plate system.

FIG. 2 is a top plan view of the embodiment of FIG. 1.

FIG. 3 is an end elevational view of the embodiment of FIG. 1.

FIG. 4 is a cross-sectional view of the embodiment of FIG. 1, taken along the lines 4-4 in FIG. 2 and viewed in the direction of the arrows.

FIG. 5 is a cross-sectional view of the embodiment of FIG. 1, taken along the lines 5-5 in FIG. 1 and viewed in the direction of the arrows.

FIG. 6 is a side elevational view of an embodiment of an orthopedic plate system.

FIG. 7 is a top plan view of the embodiment of FIG. 6.

FIG. 8 is an end elevational view of the embodiment of FIG. 6.

FIG. 11 is a side elevational view of an embodiment of an orthopedic plate system.

FIG. 12 is a top plan view of the embodiment of FIG. 11.

FIG. 13 is an end elevational view of the embodiment of FIG. 11.

FIG. 14 is a cross-sectional view of the embodiment of FIG. 11, taken along the lines 9-9 in FIG. 12 and viewed in the direction of the arrows.

FIG. 15 is a cross-sectional view of the embodiment of FIG. 11, taken along the lines 10-10 in FIG. 11 and viewed in the direction of the arrows.

DESCRIPTION OF THE ILLUSTRATED EMBODIMENTS

Figure 10:
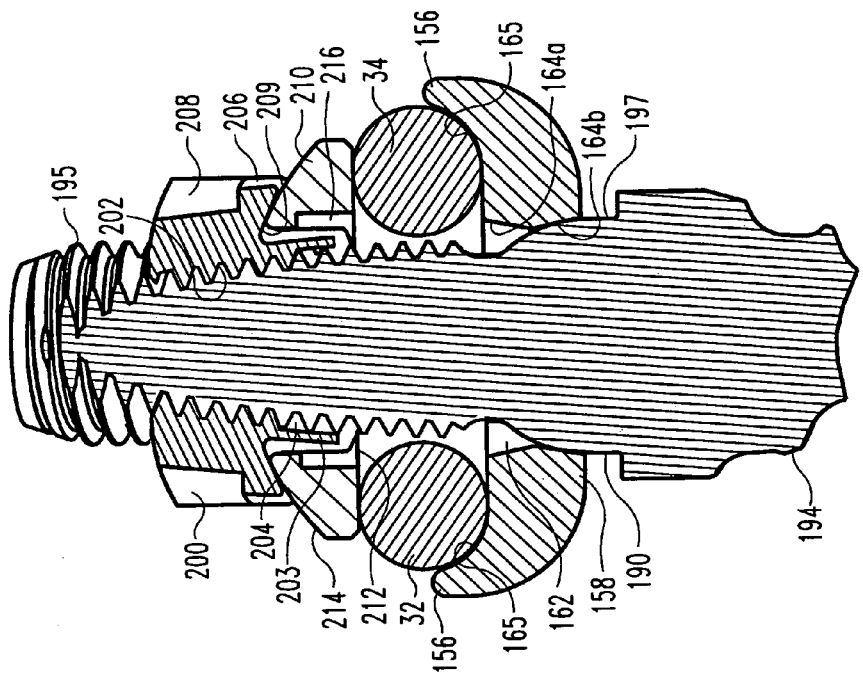
FIG. 10 is a cross-sectional view of the embodiment of FIG. 6, taken along the lines 10-10 in FIG. 6 and viewed in the direction of the arrows.
Figure 9:
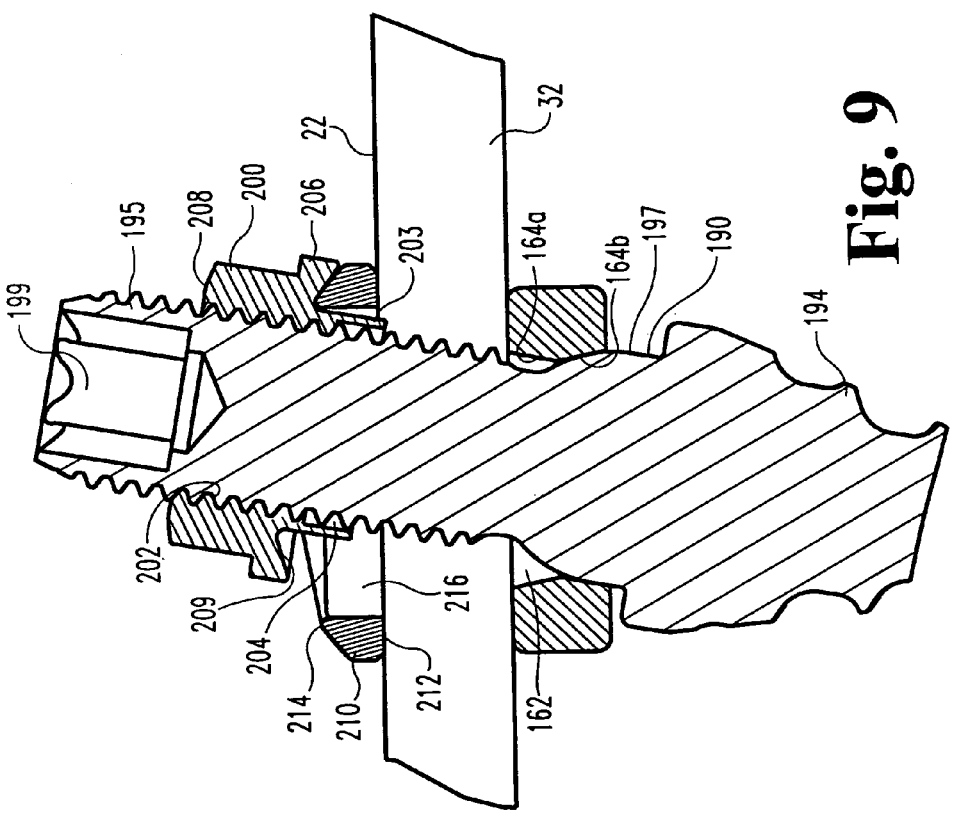
FIG. 9 is a cross-sectional view of the embodiment of FIG. 6, taken along the lines 9-9 in FIG. 7 and viewed in the direction of the arrows.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated devices, and such further applications of the principles of the disclosure as illustrated therein, being contemplated as would normally occur to one skilled in the art to which the disclosure relates.

Referring generally to FIGS. 1-5, an embodiment of an orthopedic implant system 20 is illustrated. In that embodiment, implant system 20 includes a plate member 22, at least one clamp 24, and a bone fixation member 26 connected to clamp 24. Differing numbers of any of those elements may be utilized without departing from the scope of this disclosure. For example, a plurality of plate members 22 can be used in conjunction with each other, and additional clamps 24 and bone fixation members 26 may be used, depending upon the size, shape or other configuration of the plate member, the medical problem to be addressed, and/or other factors.

In one embodiment, plate member 22 is generally in the form of an elongated oval, having a first side or rail 32, a second side or rail 34, a first end 36, and a second end 38. Sides 32, 34 and ends 36, 38 define or enclose a space 40 in the illustrated embodiment. Each of sides 32, 34 have a length between ends 36 and 38, and in a particular embodiment sides 32, 34 are substantially straight over their lengths between ends 36 and 38. Sides 32, 34 are further cylindrical, e.g. a cross-section perpendicular to a longitudinal axis of sides 32, 34 is substantially circular. Similarly, ends 36 and 38 are substantially cylindrical, e.g. a cross section perpendicular to a central axis is also substantially circular. In the illustrated embodiment, sides 32, 34 each have respective diameters that are equal to each other, and to the diameters of ends 36, 38. Thus, plate member 22 may be thought of as a single substantially cylindrical rod that is bent around into a continuous substantially oval shape so that its ends meet. It may also be thought of as two parallel cylindrical rods with ends bent to meet each other. The cylindrical shape of sides 32, 34 can make bending plate member 22 around any axis or in torsion easier due to the lack of corners or material concentrations, while not requiring the cutting, assembly and manipulation of two rods. It also enables use of plate member 22 with a variety of implants designed for use with cylindrical rods. Of course, the diameters of each side may be different from each other and/or from those of the ends, and other configuration changes may be made.

An embodiment of a clamp 24 is usable with plate member 22. The embodiment of clamp 24 shown in FIGS. 1-5 includes a yoke member 52 and a crown member 54. Yoke member 52 has an upper portion 56 that is somewhat thinner than a lower portion 58. In a particular embodiment, upper portion 56 is sized to be able to be inserted through space 40 of plate member 22, and has a threaded portion 60. In a particular embodiment, upper portion 56 has a width dimension substantially the same as the distance between the closest points of side 32 and 34 of plate member 22. Upper portion 56 may also include an opening or aperture 62. At least some of aperture 62 may include a print or profile 64 (e.g. hexagonal print, TORX print or similar surfaces) or otherwise configured for engagement by a tool. Lower portion 58 of yoke member 52, in the illustrated embodiment, has a chamber 66, a groove 68 toward the open end of chamber 66, and a beveled edge 70. Chamber 66 is sized to accommodate at least part of a bone fixation member (e.g. member 26), as further discussed below. Chamber 66 may communicate with aperture 62 in upper portion 56, and may also be open to the side of yoke member 52, having surfaces 72, 74 that generally face plate member 22. A ring member 76 is shown seated in groove 68. An internal dimension of ring member 76 when in groove 68 is smaller than an outside dimension of a portion of the fixation member in chamber 66. Ring member 76 may be substantially C-shaped with an unstressed configuration that is substantially planar or wavy, and/or that is somewhat larger than the diameter of groove 68, so that ring member 76 is held in groove 68. Alternatively, ring member 76 may have other configurations or properties, such as being made of a shape-memory material.

The illustrated embodiment of crown member 54 has an upper surface 78 through which a hole 80 extends, an internal surface 82 that may be substantially spherical, and extending fingers 84. Crown member 54 is generally sized to fit movably within chamber 66 so that ring member 76 can be between crown member 54 and beveled edge 70. Hole 80 communicates with chamber 66, and in the illustrated embodiment is substantially aligned with aperture 62 of upper portion 56 of yoke member 52. Fingers 84 of crown member 54 extend at least slightly over surfaces 72, 74 in the illustrated embodiment.

An embodiment of a bone fixation member 26 is also shown. Generally, the illustrated embodiment of bone fixation member 26 includes a head portion 90 with an internal driving print 92 such as those described above with respect to print 64, and a threaded shank portion 94. Head portion 90 is substantially spherical in part, and includes one or more ridges 96, which may be circumferential. As noted above, head portion 90 is sized to fit in chamber 66 and to be retained there by ring member 76, so that bone fixation member 26 can be multi-axially positioned with respect to yoke member 52. While bone fixation member 26 is shown in this embodiment as a screw, it may instead be a hook or other type of orthopedic implant or device.

A nut 100 is also provided in the illustrated embodiment. Nut 100 has internal threads 102, a lower opening 104 that may be beveled in part and may be substantially cylindrical in part, and may also include a widened lower part 106 that extends laterally somewhat further than an upper part 108 having external flats for driving. Upper part 108 may include a different print or configuration for driving.

In use, clamp 24 and bone fixation member 26 may be connected prior to surgery, or at any other time as may be convenient for the surgeon or others. Crown member 54 is inserted into chamber 66 of yoke 52, atop or prior to insertion of head 90 of bone fixation member 26 into chamber 66. Ring member 76 is placed around shank 94 and inserted through beveled opening 70 into chamber 66. Ring member 76 may be compressed if appropriate, for example if it is a C-shaped member with an unstressed diameter larger than the diameter of chamber 66, as noted above. Ring member 76 is advanced into chamber 66 and placed at least partially in groove 68. Thus, the illustrated embodiment places head 90 of bone fixation member 26 between ring member 76 and crown member 54 in chamber 66 of yoke member 52.

Bone fixation member 26 and clamp 24 are attached to tissue, such as vertebral bone. In one embodiment, a hole can be drilled in a vertebra of a size suited to bone fixation member 26. Threaded shank 94 is inserted into the hole, and in one embodiment a tool (not shown) with an appropriately configured tip is inserted into print 92, and where bone fixation member 26 and clamp 24 are pre-assembled, through aperture 62 of yoke member 52 and hole 80 of crown member 54 as well, and is turned to thread shank 94 into the bone. When shank 94 is threaded into the bone to the desired depth, the tool is removed from yoke member 52. Clamp 24 can be rotated and/or pivoted around head 90 of bone fixation member 26 to a relative position as may be desired by the surgeon.

Plate member 22 is then placed over clamp 24 by inserting upper portion 56 of yoke member 52 is through space 40 of plate member 22. Sides 32, 34 of plate member 22 may abut fingers 84 of crown member 54. Plate member 22 is adjusted with respect to clamp 24, and/or the combination of plate member 22 and clamp 24 are adjusted with respect to bone fixation member 26 as may be desired by the surgeon. Nut 100 is threaded onto upper portion 56 of yoke member 52 and tightened against plate member 22. Tightening nut 100 presses plate member 22 against crown member 54, and bone fixation member 26 is gripped between surface 82 of crown member 54 and ring member 76.

It will be understood that another clamp 24 and bone fixation member 26 may be placed in other tissue, such as an adjacent vertebra, and connected to plate member 22 substantially as described above. Additionally or alternatively, other types of bone implants or orthopedic devices may be connected to adjacent bone or other tissue, or may simply form a connection between plate member 22 and yet further orthopedic implants or instrumentation.

Plate member 22 may be used with a variety of clamps, bone fixation members, and other implant structures. Among these are the embodiments of a clamp 124 and a bone fixation member 126 illustrated in FIGS. 6-10. Clamp 124 includes a U-shaped yoke member 152 having a pair of legs 156 and a base 158 with an aperture 162 therethrough. Aperture 162, in the illustrated embodiment, has an upper outwardly-flared substantially conical section 164a and a lower section 164b, which may also be substantially conical and outwardly-flared, or may be substantially spherical, or otherwise configured or a combination thereof. Each leg 156 forms with base 158 a recess 165. In a particular embodiment, recesses 165 are curved, with a radius of curvature substantially equal to the radius of sides 32, 34 of plate member 22. As shown in this embodiment, recesses 165 are adjacent to or abut slightly less than one quarter of the circumference of a side of plate member 22 in one embodiment so as to make placement of plate member 22 next to yoke member 152 easier. In embodiments in which recesses 165 are adjacent to or abut somewhat more than one quarter of the circumference of a side of plate member 22, yoke member 152 may be snapped onto sides 32, 34 of plate member 22, or one of ends 36, 38 may be inserted between legs 156 and yoke member 152 can be slid along plate member 22 to a desired relative location.

Bone fixation member 126 is a bolt having a medial head portion 190 between a threaded shank 194 for connection to tissue such as vertebral bone and an upper threaded portion 195. Examples of such bolts are disclosed in U.S. Pat. No. 6,280,445, which is incorporated herein by reference in its entirety. Head portion 190 may have a substantially spherical upper portion 197 that abuts and is pivotable with respect to lower aperture section 164b. Upper threaded portion 195 includes an internal print 199 for driving bone fixation member 126. Print 199 may be configured as described above with respect to prints 64 and 92.

Nut 200 is also shown in this embodiment. Nut 200 is similar to that disclosed in U.S. Pat. No. 6,315,779, which is incorporated herein by reference in its entirety. The illustrated embodiment of nut 200 includes internal threads 202, a lower cylindrical skirt 203 surrounding a lower opening 204, and a widened lower part 206 that extends laterally somewhat further than an upper part 208 having external flats for driving. Upper part 108 may include a different print or configuration for driving. An underside 209 of nut 200 is outwardly-flared and may be substantially conical. In addition to nut 200, a washer 210 may be provided having a flat underside 212, a curved or conical upper side 214, and a hole or slot 216 that permits upper threaded portion 195 of bone fixation member 126 to move in at least one plane with respect to washer 210. Nut 200 and washer 210, if used together, may form a pre-assembled unit, and skirt 203 may be swaged or otherwise expanded to prevent nut 200 from being removed from washer 210 while preserving the ability of nut 200 to move along and rotate with respect to washer 210.

In use, clamp 124 may be connected to either or both of bone fixation member 126 and plate member 22 prior to surgery, or at any other time as may be convenient for the surgeon or others. In one embodiment, bone fixation member 126 is attached to tissue, such as vertebral bone. For example, a hole can be drilled in a vertebra of a size suited to threaded shank 194 of bone fixation member 26. Threaded shank 194 is inserted into the hole, and in one embodiment a tool (not shown) with an appropriately configured tip is inserted into print 192, and is then turned to thread shank 194 into the bone. When shank 194 is threaded into the bone to the desired depth, the tool is removed.

Clamp 124, if not previously connected, is placed on bone fixation member 126 so that upper threaded portion extends above clamp 124 and medial head 190 abuts clamp 124, for example at least partially within aperture portion 162*b*. Clamp 124 can be rotated and/or pivoted around head 190 of bone fixation member 126 to a relative position as desired by the surgeon. Plate member 22, if not previously connected to clamp 124, may be placed over bone fixation member 126 and adjacent to clamp 124. In that position, sides 32, 34 of plate member 22 are at least partially within recesses 165 of clamp 124, and upper threaded portion 195 of bone fixation member 126 extends through space 40 of plate member 22.

Plate member 22 and clamp 124 can be adjusted with respect to bone fixation member 126, at least by pivoting bone fixation member 126 along the plane of slot 216 and/or the length of plate member 22, as may be desired by the surgeon. Nut 200 and washer 210 are placed over upper threaded portion 195 of bone fixation member 126, and nut 200 is threaded down and tightened so as to press washer 210 against plate member 22. Tightening nut 100 also pulls bone fixation member 126 so that its head 190 presses clamp 124 against plate member 22, locking the construct. It will be understood that nut 200 could be used without washer 210, or with a different washer. It will further be understood that nut 100, with or without a washer such as washer 210, or another type of nut could be used with fixation member 126 in other embodiments. For example, a nut such as nut 200' (FIGS. 11-15) may be provided with a substantially flat bottom. Locking plate member 22, clamp 124 and bone fixation member 126 with a nut such as nut 200' substantially limits or inhibits planar or multi-axial positioning of bone fixation member 126 with respect to clamp 124 and plate member 22.

Figure 16:
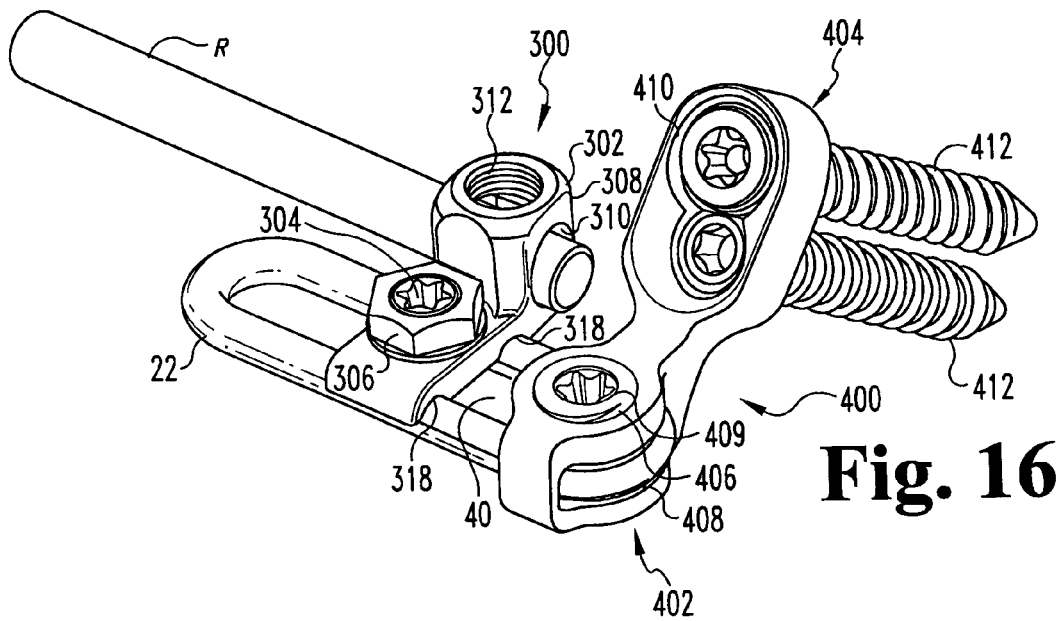
FIG. 16 is a perspective view of an embodiment of an orthopedic plate system.
Figure 16A:
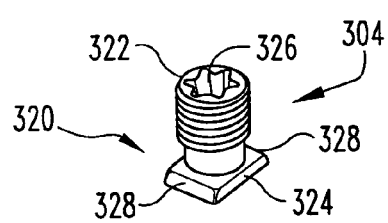
FIG. 16A is a perspective view of an apparatus that may be used with the embodiment of FIG. 16.
Figure 17:
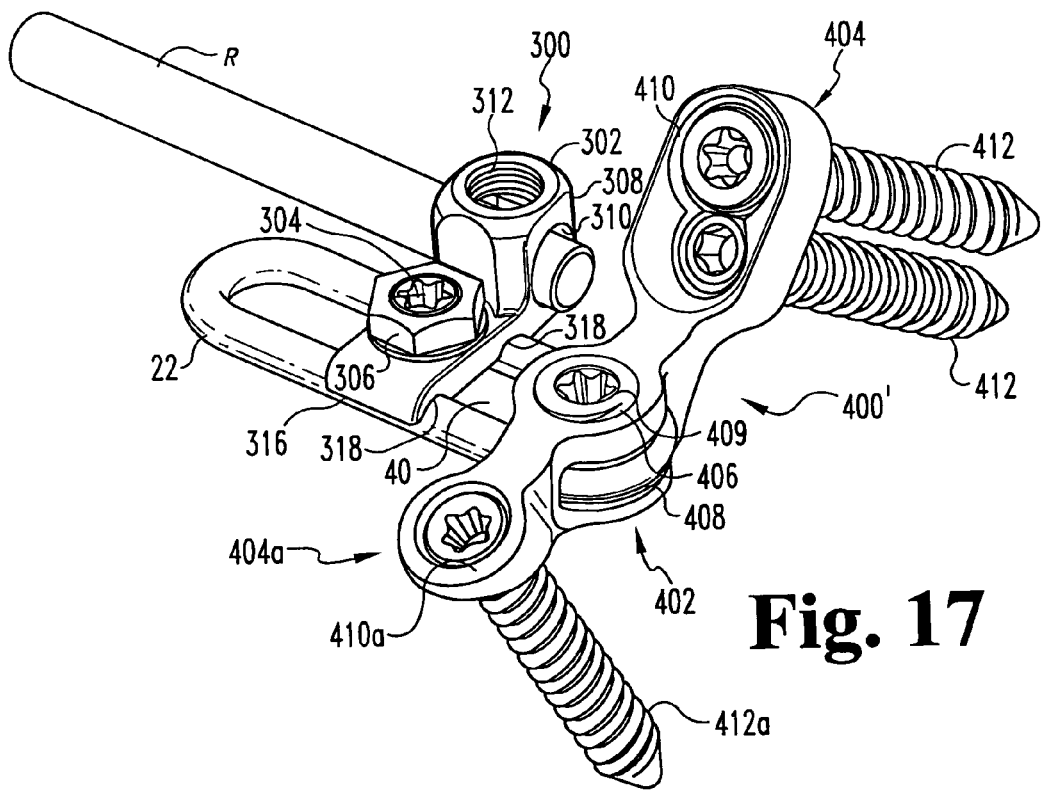
FIG. 17 is a perspective view of an embodiment of an orthopedic plate system.

Additional parts may be provided individually or as a kit with embodiments as described above or other embodiments. For example, as shown in FIGS. 16-17, a lateral connector 300 is shown connected to plate member 22. Connector 300 includes a connecting member 302, a post 304, and a nut 306. Connecting member 302 includes a block portion 308 having a first opening 310 therethrough for accommodating at least part of an elongated member such as orthopedic rod R, and a second opening 312 that is threaded for a set screw (not shown) that locks elongated member R with respect to block portion 308. Connecting member 302 further includes an extension portion 316 that extends laterally from block portion 308, and in a particular embodiment extension portion 316 is substantially perpendicular to a surface of block portion 308. In the illustrated embodiment, one side of extension portion 316 includes two recesses 318, which may have a substantially cylindrical shape and may have a diameter substantially the same as the diameter of sides 32, 34 of plate member 22. Recesses 318 are for accommodating at least a portion of sides 32, 34 of plate member 22, and in one embodiment walls of recesses 318 contact respective sides 32, 34 of plate member 22. As seen in the embodiment of FIGS. 16-17, recesses 318 are on a side of extension portion 316 that essentially faces away from block portion 308 and elongated member R. It will be understood that recesses 318 could be on either side of extension portion 316. A hole is provided through extension portion 316 between recesses 318.

Post 304, in the illustrated embodiment, includes a body 320 with a substantially cylindrical upper portion 322 and a lower flange 324. Upper portion 322 may be threaded and include a print 326, such as an internal hexagonal, TORX, or other configuration, for accommodating a tool. Flange 324 extends generally laterally from body 320, although it could extend around other portions of the perimeter of body 320, or the entire perimeter of body 320. In a particular embodiment, flange 324 has end portions 328 that are obliquely angled with respect to the rest of flange 324, and may be substantially planar, may form part of a spherical surface, or may be otherwise configured. As will be discussed further below, flange 324 is sized so that at least part of end portions 328 can abut portions of sides 32, 34 of plate member 22. Nut 306 is internally threaded and sized to be threaded onto the upper portion 322 of post 304.

Connector 300 can be connected to plate member 22 prior to surgery or during a surgical procedure, as may be convenient for the surgeon. Extension portion 316 is placed over or under plate member 22 so that sides 32, 34 of plate member 22 are at least partially in recesses 318 of extension portion 316. Upper portion 322 of post 304 is inserted through space 40 of plate member 22 and hole 319 so that end portions 328 of flange 324 are adjacent to or abutting sides 32, 34 of plate member 22. Nut 306 is threaded onto post 304 and tightened against extension portion 316 (in the illustrated embodiment) to lock plate member 22 between extension portion 316 and flange 324. Alternatively, connector 300 could be connected underneath plate member 22 (i.e. opposite to what is shown in FIGS. 16-17), and nut 306 may directly contact plate member 22 and flange 324 abut extension portion 316. Plate member 22 may be locked between nut 306 and flange 324. An elongated member R, such as a spinal rod, is inserted into block portion 308 and locked by a set screw (not shown) either prior to or after connection of connector 300 to plate member 22.

Another apparatus that may be connected to plate member 22 are embodiments of additional connecting or stabilizing members, such as the embodiment of a connecting plate 400 shown in FIG. 16. In that embodiment, connecting plate 400 includes a joining portion 402 for attaching to plate member 22 and a plate portion 404 for connecting to other tissue or devices, for example sacral bone or apparatus implanted in sacral bone. Joining portion 402 includes a hole 406 therethrough and a slot 408 therethrough, where slot 408 is in a plane substantially perpendicular to the axis of hole 406. Slot 408 has a width sufficient to allow plate member 22 to pass through, so that space 40 of plate member 22 and hole 406 communicate. If hole 406 is internally threaded, a set screw 409 may be provided to lock joining portion 402 with respect to plate member 22. Alternatively, regardless of whether hole 406 is threaded, post 304 and nut 306 may be provided and used to lock joining portion 402 with respect to plate member 22, substantially as discussed above with respect to connecting member 300 and plate member 22.

Plate portion 404, in the illustrated embodiment, has at least one hole 410 therethrough, which may be adapted to receive a bone screw that is implanted into sacral or other bone, or may be adapted to receive other types of orthopedic implants or instrumentation. In the embodiment of FIG. 16, two bone screws 412 extend through one or more holes 410. It will be understood that a bone screw through plate portion 404 could be provided, with a separate threaded hole for a set screw, the head of which overlaps the head of the bone screw to inhibit loosening or pulling out of the bone screw from bone. Plate portion 404 and joining portion 402 can be oriented with respect to each other as may be warranted for certain orthopedic corrective procedures or anatomic placements. For example, the illustrated embodiment of connecting plate 400 shows plate portion 404 to be non-planar with joining portion 402, and an obtuse angle is formed between them. Such a construct may be useful with a plate member 22 that is connected to lower lumbar or sacral vertebra(e) (such as L5 or S1), which the surgeon also desires to connect laterally to sacral or other bone. The angle between joining portion 402 and plate portion 404 may vary (as by bending connecting plate 400 or by providing variously angled connecting plates 400 in a kit) to most closely meet the anatomic conditions or needs of the patient. In other embodiments, plate portion 404 and joining portion 402 may be substantially planar with respect to each other, may be twisted so that they are non-planar but share a longitudinal axis, or otherwise configured.

Connecting plate 400 may be connected to plate 22 prior to surgery or during a surgical procedure, as may be convenient for the surgeon. An end 36 or 38 of plate member 22 is inserted through slot 408 of joining portion 402 so that connecting plate 400 is positioned on plate member 22 as the surgeon desires. Where hole 406 is threaded and a screw 409 is provided, screw 409 is threaded into hole 406 and against plate member 22, pressing plate member 22 against joining portion 402 to lock them together. If post 304 and nut 306 are used, upper portion 322 of post 304 is inserted through hole 406 of joining portion 402 and through space 40 of plate member 22 so that flange 324 is adjacent to or abutting joining portion 402, and upper portion 322 extends from joining portion 402. Nut 306 is threaded onto post 304 and tightened against joining portion 402, squeezing slot 408 to lock plate member 22 therein. Alternatively, hole 406 and/or flange 324 could be sized so that flange 324 can fit through at least part of hole 406 and end portions 328 of flange 324 are adjacent to or abut sides 32, 34 of plate member 22. Tightening nut 306 against joining portion 402 causes plate member 22 to be gripped between flange 324 and joining portion 402. Plate portion 404 can be connected to tissue or other implants or apparatus before or after connecting joining portion 402 to plate member 22. However, insofar as plate member 22 is movable in one or more directions prior to its fixation to bone or other tissue, it may be somewhat easier to use connecting plate 400 if it is first connected by plate portion 404 to tissue or apparatus, and then connected to plate member 22.

Referring now generally to FIG. 17, there is shown another embodiment of a connecting plate 400' connected to plate member 22. Connecting plate 400' is substantially the same as connecting plate 400, with the addition of a second plate portion 404a. In this embodiment, joining portion 402 is between plate portions 404 and 404a, and plate portion 404a is angled with respect to joining portion 402 so that plate portions 404 and 404a are non-planar but substantially parallel. Plate portion 404a includes a hole 410a through which a screw 412a or other implant or device can extend, for example into bone. Other aspects described above with respect to plate portion 404 may also be found in plate portion 404a.

It will be seen that the parts shown in various drawings are not limited to use with the embodiments with which they are illustrated or specifically described, but may be used with or combined with other embodiments. Thus, for example, one plate member 22 may be used with one clamp 24 and one clamp 124, and parts shown with respect to clamp 24 could be used with clamp 124.

The parts of the implant system of the present invention may be made available in the form of kits containing a plurality of sizes and configurations of a single part, or a plurality of sizes and configurations of all parts that can be included in the system of the present invention. Such kits may include, for example, a set of elongated members 22 and/or 100 of various lengths and having differing numbers or orientations of slots and/or bores. In the case of elongated member 100, a kit could include a set of elongated member having varying degrees of bend along longitudinal axis 106. Sets of washers, bolts, screws and nuts as disclosed herein can also be provided. Further, tools such as wrenches and screwdrivers compatible with the parts of the implant system of the present invention may also be included.

The devices of the present invention are preferably constructed of sturdy bio-compatible materials, such as stainless steel, titanium, certain plastics, or other known materials.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus comprising:
a plate member having first and second substantially circular cylindrical sides each defining a circular outer cross-section and said plate member also having first and second ends, said sides and said ends defining an enclosed space;
a clamp adjacent said plate member, said clamp having a first recess for accommodating at least a portion of said first side of said plate member, and a second recess for accommodating at least a portion of said second side of said plate member, wherein said clamp includes a substantially U-shaped member having a first leg, a second leg, and a base portion, said base portion having a hole therethrough having an upper outwardly-flared substantially conical section and a lower section, the upper section being disposed adjacent the first and second recesses;

a bone fixation member connected to said clamp, said bone fixation member including a head portion and a bone engaging portion extending from said head portion; and a single locking member adapted to hold said plate member to said clamp and said bone fixation member in a locked construct, wherein said single locking member presses said head portion of said bone fixation member against said clamp and also presses said clamp against said plate member to provide said locked construct.

2. The apparatus of claim 1, wherein said first recess is defined at least partially by said first leg and said base portion, and said second recess is defined at least partially by said second leg and said base portion.

3. The apparatus of claim 1, wherein said first side of said plate member has a diameter and said second side of said plate member has a diameter, and said first recess has a portion with a diameter substantially equal to said diameter of said first side of said plate member, and said second recess has a portion with a diameter substantially equal to said diameter of said second side of said plate member.

4. The apparatus of claim 1, further comprising:

a lateral connecting member having a block portion and an extension portion, said block portion having a first aperture accommodating an elongated member and a second aperture for accommodating a screw for forcing the elongated member away from said second aperture to lock the elongated member in said block portion, said extension portion having a first recess for accommodating at least a portion of said first side of said plate member, a second recess for accommodating at least a portion of said second side of said plate member, and a hole between said recesses of said lateral connecting member;

a post member having a threaded portion and a flange portion, said post member extending through said space of said plate member and said hole of said extension portion of said lateral connecting member so that said flange portion is adjacent said plate member, and a nut threaded onto said threaded portion of said post member, whereby said lateral connecting member is locked between said nut and said flange portion of said post member.

5. The apparatus of claim 1, wherein said bone fixation member includes an upper threaded portion extending from said head portion, and wherein said upper threaded portion of said bone fixation member extends through said hole of said U-shaped member and through said enclosed space of said plate member.

6. The apparatus of claim 5, wherein said upper threaded portion, said head portion and said bone engaging portion are integral with one another to provide said bone fixation member as a single-piece element.

7. The apparatus of claim 6, wherein tightening of said nut onto said upper threaded portion of said bone fixation member pulls said head portion of said bone fixation member toward said plate member and presses said head portion against said base portion of said clamp and also presses said clamp against said plate member to provide a locked construct.

8. The apparatus of claim 6, further comprising a washer positioned over said upper threaded portion of said bone fixation member between said nut and said plate member, and wherein tightening of said nut onto said upper threaded portion of said bone fixation member compresses said washer against said plate member.

9. The apparatus of claim 8, wherein said nut includes a flared underside and said washer includes a flared upper side, said flared underside of said nut engaged with said flared upper side of said washer.

10. The apparatus of claim 5, wherein said locking member comprises a nut, said nut threaded onto said upper threaded portion of said bone fixation member.

11. The apparatus of claim 1, wherein said first and second sides each have a circular outer surface defining said circular outer cross-section, said circular outer surface defining a substantially uniform outer diameter.

12. The apparatus of claim 1, wherein said first and second ends each have a circular outer surface defining a circular outer cross-section, said circular outer surface defining a substantially uniform outer diameter.

13. An apparatus comprising:

a plate member having first and second substantially circular cylindrical sides each defining a circular outer cross-section and said plate member also having first and second ends, said sides and said ends defining an enclosed space;

a clamp adjacent said plate member, said clamp having a first recess for accommodating at least a portion of said first side of said plate member, and a second recess for accommodating at least a portion of said second side of said plate member;

a bone fixation member connected to said clamp; and a locking member adapted to hold said plate member to said clamp and said bone fixation member; and wherein said clamp member includes a substantially U-shaped member having a first leg, a second leg, and a base portion, said base portion having a hole therethrough having an upper outwardly-flared substantially conical section and a lower section, the upper section being disposed adjacent the first and second recesses, wherein said first recess is defined at least partially by said first leg and said base portion, and said second recess is defined at least partially by said second leg and said base portion; and wherein said bone fixation member includes a bolt having a first threaded portion for connection to a bone, a medial head, and a second threaded portion, and wherein said second threaded portion extends through said hole of said U-shaped member and said space of said plate member.

14. The apparatus of claim 13, wherein said locking member comprises a nut;

wherein said nut is threaded onto said second threaded portion of said bolt; and wherein tightening of said nut onto said second threaded portion pulls said medial head of said bolt toward said plate member.

15. The apparatus of claim 13, wherein said locking member comprises a nut and a washer, said washer being between said nut and said plate member.

16. The apparatus of claim 13, wherein said first and second threaded portions of said bone fixation member are integral with said head portion to provide said bolt as a single-piece element.

17. The apparatus of claim 13, wherein said locking member comprises a nut, said nut threaded onto said second threaded portion of said bolt; and wherein tightening of said nut onto said second threaded portion pulls said medial head of said bolt toward said plate member and presses said medial head against said base portion of said clamp and also presses said clamp against said plate member to provide a locked construct.

18. The apparatus of claim 17, further comprising a washer positioned over said second threaded portion of said bolt between said nut and said plate member, and wherein tightening of said nut onto said second threaded portion of said bolt compresses said washer against said plate member.

19. The apparatus of claim 13, wherein said first and second sides each have a circular outer surface defining said circular outer cross-section, said circular outer surface defining a substantially uniform outer diameter.

20. The apparatus of claim 13, wherein said first and second ends each have a circular outer surface defining a circular outer cross-section, said circular outer surface defining a substantially uniform outer diameter.

21. An apparatus comprising:
a plate member having first and second substantially cylindrical sides and first and second ends, said sides and said ends defining an enclosed space;
a clamp adjacent said plate member, said clamp having a first recess for accommodating at least a portion of said first side of said plate member, and a second recess for accommodating at least a portion of said second side of said plate member;
a bone fixation member connected to said clamp;
a locking member adapted to hold said plate member to said clamp and said bone fixation member;
a lateral connecting member having a joining portion and at least one plate portion, said joining portion having a hole therethrough and a slot therethrough substantially perpendicular to said hole, said slot having a first surface through which said hole extends, a second surface positioned opposite said first surface, and a width sufficient to allow said plate member to pass through said slot, said plate portion having at least one hole therethrough adapted to receive a bone screw therethrough; and
a screw threaded into said hole of said joining portion and into contact against said plate member, whereby said contact applies a force on said plate member in a direction opposite of said first surface to lock said joining portion and said plate member together.

22. The apparatus of claim 21, wherein said joining portion is angled with respect to said plate portion and said hole through said joining portion extends along a first axis and said hole through said plate portion extends along a second axis that is angled relative to said first axis.

23. An apparatus comprising:
a plate member having first and second substantially cylindrical sides and first and second ends, said sides and said ends defining an enclosed space;
a clamp adjacent said plate member, said clamp having a first recess for accommodating at least a portion of said first side of said plate member, and a second recess for accommodating at least a portion of said second side of said plate member;
a bone fixation member connected to said clamp;
a locking member adapted to hold said plate member to said clamp and said bone fixation member;
a lateral connecting member having a joining portion positioned between a first plate portion and a second plate portion, said joining portion having a hole therethrough and a slot therethrough substantially perpendicular to said hole, said slot having a width sufficient to allow said plate member to pass through said slot, said plate portions each having at least one hole therethrough adapted to receive a bone screw therethrough;
a post member having a threaded portion and a flange portion, said post member extending through said space of said plate member and said hole of said joining portion of said lateral connecting member so that said flange portion is adjacent said joining portion; and
a nut threaded onto said threaded portion of said post member, whereby said lateral connecting member is locked between said nut and said flange portion of said post member.

\* \* \* \* \*